United States Patent [19]

Dean

[11] Patent Number: 4,612,185
[45] Date of Patent: Sep. 16, 1986

[54] METHODS AND COMPOSITIONS FOR ENHANCING MAGNETIC RESONANCE IMAGING

[75] Inventor: Richard T. Dean, Chesterfield, Mo.
[73] Assignee: Mallinckrodt, Inc., St. Louis, Mo.
[21] Appl. No.: 660,642
[22] Filed: Oct. 15, 1984
[51] Int. Cl.$^4$ .............................................. G01N 1/00
[52] U.S. Cl. .................................. 424/2; 260/501.12; 562/449; 562/450
[58] Field of Search ............................. 562/449, 450; 260/501.12; 424/2, 5, 4

[56] References Cited

U.S. PATENT DOCUMENTS 2,135,474 11/1938 Sachs ................................. 562/449
3,859,429 1/1975 Elias ................................. 562/449

OTHER PUBLICATIONS

Sherman, Chem. Abst., vol. 89, #99664s (1978).
Sherman et al, Chem. Abst., vol. 87, #126884f (1977).
Gal et al, Chem. Abst., vol. 90, #173s (1979).
Damadian, Science, vol. 171, pp. 1151-1153 (1971).

Primary Examiner—James H. Reamer
Attorney, Agent, or Firm—Senniger, Powers, Leavitt and Roedel

[57] ABSTRACT

Water soluble, substantially nontoxic salts of compounds of the formula:

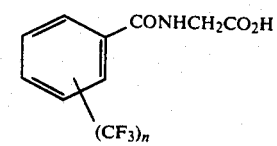

wherein $n=1$ to 5, are useful as fluorine magnetic resonance imaging agents for enhancing images of body organs and tissues. An illustrative salt of such compounds is sodium [2-(trifluoromethyl)benzamido]acetate.

10 Claims, No Drawings

METHODS AND COMPOSITIONS FOR ENHANCING MAGNETIC RESONANCE IMAGING

BACKGROUND OF THE INVENTION

This invention relates to magnetic resonance imaging (MRI), also referred to as nuclear magnetic resonance (NMR) imaging, and more particularly, to methods and compositions for enhancing magnetic resonance images of body organs and tissues.

The recently developed techniques of MRI or NMR imaging encompasses the detection of certain atomic nuclei utilizing magnetic fields and radio-frequency radiation. It is similar in some respects to X-ray computed tomography (CT) in providing a cross-sectional display of the body organ anatomy with excellent resolution of soft tissue detail. In current use, the images produced constitute a map of the distribution density of protons and/or their relaxation times in organs and tissues. The MRI technique is advantageously non-invasive as it avoids the use of ionizing radiation.

While the phenomenon of NMR was discovered in 1945, it is only relatively recently that it has found application as a means of mapping the internal structure of the body as a result of the original suggestion of Lauterbur (Nature, 242, 190–191, 1973). The fundamental lack of any known hazard associated with the level of the magnetic and radio-frequency fields that are employed renders it possible to make repeated scans on vulnerable individuals. Additionally, any scan plane can readily be selected including transverse, coronal, and sagittal sections.

In an NMR experiment, the nuclei under study in a sample (e.g. protons) are irradiated with the appropriate radio-frequency (RF) energy in a highly uniform magnetic field. These nuclei as they relax subsequently emit RF radiation at a sharp resonant frequency. The emitted frequency (RF) of the nuclei depends on the applied magnetic field.

According to known principles, nuclei with appropriate spin when placed in an applied magnetic field [B, expressed generally in units of gauss or tesla ($10^4$ gauss)] align in the direction of the field. In the case of protons, these nuclei precess at a frequency $f = 42.6$ MHz at a field strength of 1 Tesla. At this frequency, an RF pulse of radiation will excite the nuclei and can be considered to tip the net magnetization out of the field direction, the extent of this rotation being determined by the pulse duration and energy. After the RF pulse, the nuclei "relax" or return to equilibrium with the magnetic field, emitting radiation at the resonant frequency. The decay of the signal is characterized by two relaxation times, i.e., $T_1$, the spin-lattice relaxation time or longitudinal relaxation time, that is, time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In MRI, scanning planes and slice thickness can be selected. This permits high quality transverse, coronal and sagittal images to be obtained directly. The absence of any moving parts in MRI equipment promotes a high reliability. It is believed that MRI or NMR imaging has a greater potential than CT for the selective examination of tissue characteristics in view of the fact that in CT, X-ray attenuation coefficients alone determine image contrast whereas at least four separate variables ($T_1$, $T_2$, nuclear spin density and flow) may contribute to the NMR signal. For example, it has been shown (Damadian, Science, 171, 1151, 1971) that the values of the $T_1$ and $T_2$ relaxation in tissues are generally longer by about a factor of 2 in excised specimens of neoplastic tissue compared with the host tissue.

By reason of its sensitivity to subtle physio-chemical differences between organs and/or tissues, it is believed that MRI may be capable of differentiating tissue types and in detecting diseases which induce physio-chemical changes that may not be detected by X-ray or CT which are only sensitive to differences in the electron density of tissue. The images obtainable by MRI techniques also enable the physician to detect structures smaller than those detectable by CT and thereby provide comparable or better spatial resolution.

SUMMARY OF THE INVENTION

Among the several objects of the invention may be noted the provision of novel compounds and compositions containing fluorine-19 for enhancing magnetic resonance images of body organs and tissues; the provision of such compounds and compositions which comprise water soluble, substantially non-toxic salts of certain trifluoromethylbenzamidoacetic acid compounds; and the provision of methods for enhancing fluorine-19 magnetic resonance images of body organs and tissues through the administration of such compounds and compositions. Other objects and features will be in part apparent and in part pointed out hereinafter.

Briefly, the invention is directed to compounds of the formula:

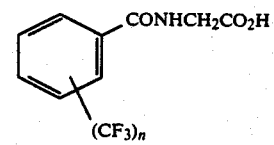

wherein $n = 1$ to 5, and water soluble, substantially non-toxic salts thereof with pharmaceutically acceptable cations. The invention is also directed to methods for enhancing magnetic resonance images of body organs and tissues by administering such salts to a mammal in sufficient amounts to provide enhancement of fluorine-19 magnetic resonance images of the body organs and tissues.

DESCRIPTION OF THE PREFERRED EMBODIMENTS

The evaluation of blood flow and perfusion in tissues by imaging techniques is of physiologic and diagnostic importance. While $^1$H magnetic resonance imaging has shown some promise for evaluation of blood flow in linear portions of large vessels, no demonstration of tissue perfusion has been made with $^1$H MRI.

Fluorine atoms ($^{19}$F) give a clear nuclear magnetic resonance signal and thus may function as suitable "probes" in MRI when combined in a chemically suitable form. The specific advantages flowing from the use of $^{19}$F are: (1) its low intrinsic concentration in soft tissues of the body; (2) its high nuclear magnetic resonance sensitivity, and (3) a magnetogyric ratio which is close to that of $^1$H, thereby making the observation of $^{19}$F tractable with existing RF components.

In accordance with the present invention, it has now been found that the water soluble, substantially nontoxic salts of benzamidoacetic acid (also known as hippuric acid) compounds containing trifluoromethyl groups are useful as fluorine ($^{19}$F) MRI agents, particularly for use in evaluating blood flow, perfusion and renal excretion. The benzamidoacetic acid compounds are those of the following formula:

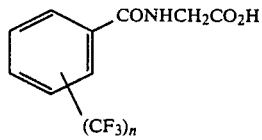

wherein n=1 to 5. Specific examples of such compounds include 2-(trifluoromethyl)benzamidoacetic acid, 3-(trifluoromethyl)benzamidoacetic acid, 4-(trifluoromethyl)benzamidoacetic acid, 2,3-bis(trifluoromethyl)benzamidoacetic acid, 3,4,5-tris(trifluoromethyl)benzamidoacetic acid, 3,5-bis(trifluoromethyl)benzamidoacetic acid and 2,4,5-tris(trifluoromethyl)benzamidoacetic acid.

Water soluble, substantially nontoxic salts of such trifluoromethyl benzamido acetic acid compounds with pharmaceutically acceptable cations conventionally used, for example, with intravenous ionic X-ray contrast agents, such as the sodium, N-methylglucamine and diethanolamine salts, are suitable for use as fluorine MRI agents in the practice of the invention. Solutions of such salts may, for example, be administered intravenously to a mammal in a sufficient amount to provide enhancement of images of body organs and tissues by MRI techniques prior to obtaining a proton scan or scans of such organs and tissues. Illustrative salts of the novel trifluoromethylbenzamidoacetic acid compounds which may be used in carrying out the invention include sodium [2-(trifluoromethyl)benzamido]acetate, N-methylglucaminium [2-(trifluoromethyl)benzamido]acetate, sodium [2,3-bis(trifluoromethyl)benzamido]acetate and N-methlyglucaminium [3-(trifluoromethyl)benzamido]acetate. Other salts of the aforementioned trifluoromethylbenzamidoacetic acid compounds may also be employed.

As shown by the toxicity studies set forth hereinafter, a representative member of the class of trifluoromethylbenzamidoacetic acid compounds herein contemplated, namely, sodium [2-(trifluoromethyl)benzamido]acetate, possesses an extremely good intravenous toxicity profile. Also, based upon its tissue distribution in MRI studies, this compound is indicated for usage as a fluorine MRI agent for evaluating blood flow, perfusion and renal excretion.

The following examples illustrate the practice of the invention.

EXAMPLE 1

Preparation of 2-(trifluoromethyl)benzamidoacetic acid

In a 500 ml, 3-necked flask was dissolved glycine (9.03 g) in water (50 ml). The flask was cooled in an ice/methanol bath. Sodium hydroxide (12.6 g) in 30 cc of water was added. 2-Trifluoromethylbenzoyl chloride (25 g) was added at a temperature below 0° C. The bath was removed and the reaction mixture stirred for 2.5 hours at room temperature. To this was added concentrated HCl until the pH was 1. The solid was collected by filtration, washed with water and dried to give 25 g(84%), m.p. 147°–149° C. The product was a single spot by thin layer chromatography. (n-butyl alcohol:isopropyl alcohol:NH$_4$OH; 10:4:4).

Elemental Analysis Results: Calculated for C$_{10}$H$_8$F$_3$NO$_3$: C, 48.58; H, 3.23; N,5.60. Found: C, 48.80; H, 3.22; N, 5.46.

EXAMPLE 2

Sodium [2-(trifluoromethyl) benzamido] acetate was prepared as a 20% w/v solution in sterile water for injection and the pH was adjusted to 7.0 using 0.1 N HCl.

A total of 14 mice (7 male, 24.6–30.0 g; 7 females, 18.6–26.0 g; Swiss ICR CD-1, Charles River) were used. Animals were housed according to standard operating procedures and marked for identification with picric acid.

Groups of 2–3 mice received single intravenous injections of sodium [2-(trifluoromethyl)benzamido]acetate according to the following schedule:

| COMPOUND DOSE | | | NUMBER OF MICE | |
|---|---|---|---|---|
| mg/kg | mg F/kg | mmol F/kg | MALE | FEMALE |
| 1000 | 212 | 11.2 | 1 | 1 |
| 2000 | 424 | 22.3 | 1 | 1 |
| 4000 | 847 | 44.6 | 1 | 1 |
| 6000 | 1271 | 66.9 | 1 | 2 |
| 7000 | 1483 | 78.1 | 2 | 1 |
| 8000 | 1694 | 89.2 | 1 | 1 |

Measured single doses were injected into the lateral tail vein at a rate of 1 ml/min. The animals were observed immediately after dosing and during the 7-day observation period for pharmacotoxic reactions. Recording of terminal body weights and general necrospy of the thoracic and abdominal organs was performed after 7 days. An LD$_{50}$ value was calculated using the method of Litchfield and Wilcoxon (J. Pharmacol. Exp. Ther. 96:99,1949).

The data are summarized as follows:

| COMPOUND DOSE (mg/kg) | MORTALITIES/ NUMBER TREATED | AVERAGE SURVIVOR WEEKLY BODY WEIGHT CHANGE (g) |
|---|---|---|
| 1000 | 0/2 | 0.1 |
| 2000 | 0/2 | 2.2 |
| 4000 | 0/2 | 1.8 |
| 6000 | 1/3 | 1.0 |
| 7000 | 2/3 | 2.7 |
| 8000 | 2/2 | — |

Following intravenous administration of sodium [2-(trifluoromethylbenzamido]acetate, toxic reactions consisted of mild hyperactivity at doses=2000 mg/kg and dose-related hypoactivity at doses=4000 mg/kg. All deaths occurred within 10 minutes of treatment and were preceded by mild convulsions. All survivors appeared normal within 5 hours after treatment. One survivor dosed with 1000 mg of the compound exhibited body weight loss the week after treatment, whereas all other survivors exhibited weight gains. No abnormalities were observed upon necropsy following the one week observation period.

Sodium [2-(trifluoromethyl)benzamido]acetate had an estimated mouse intravenous LD$_{50}$ of 6500 mg/kg which corresponds to a fluorine dose of 72 mmol F/kg (1377 mg F/kg).

EXAMPLE 3

An anesthetized rabbit was placed in a 12 inch bore, 1.9 Tesla MRI magnet. An RF coil (317 cm, I.D., 4 cm, O.D.) was placed on the surface of the liver or a kidney which were excised surgically. Fluorine spectra were obtained following 4 mmol F/kg intravenous doses of a solution of sodium [2-(trifluoromethyl)benzamido]acetate (20%, w/v, 2.2 M F, of the compound). In both liver and kidney, fluorine spectra contained only a single peak which was the same as the spectrum from a solution of sodium [2-(trifluoromethyl)benzamido]acetate. The fluorine signal intensity peaked very rapidly in the kidney and remained elevated for several minutes. The liver signal intensity was less than that for the kidney and took a longer time to peak.

At the conclusion of the experiment, the rabbit was killed and liver, heart, kidney, skeletal muscle, spleen, blood and urine samples were analyzed for fluorine by MR spectroscopy. The highest concentrations of fluorine were detected in kidney, urine and blood specimens with minimal fluorine detected in other tissue specimens.

As various changes could be made in the above compositions and methods without departing from the scope of the invention, it is intended that all matter contained in the above description shall be interpreted as illustrative and not in a limiting sense.

What is claimed is:

1. A composition for enhancing fluorine-19 magnetic resonance images of body organs and tissues, the composition comprising a water soluble, substantially nontoxic salt of a compound of the formula:

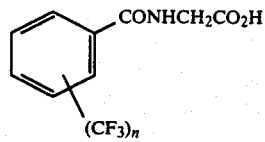

wherein n=1 to 5.

2. A composition as set forth in claim 1 wherein said salt is a sodium or N-methylglucamine salt of said compound.

3. A composition as set forth in claim 1 wherein said compound is 2-(trifluoromethyl)benzamidoacetic acid.

4. Sodium [2-(trifluoromethyl)benzamido]acetate.

5. A method for enhancing fluorine-19 magnetic resonance images of body organs and tissues which comprises administering to a mammal a composition comprising a water soluble, substantially nontoxic salt of a compound of the formula:

wherein n=1 to 5, in a sufficient amount to provide enhancement of magnetic resonance images of said body organs and tissues.

6. A method as set forth in claim 5 wherein said salt is a sodium or N-methylglucamine salt of said compound.

7. A method as set forth in claim 5 wherein said compound is 2-(trifluoromethyl)benzamidoacetic acid.

8. A method as set forth in claim 5 wherein said composition is sodium [2-(trifluoromethyl)benzamido]acetate.

9. A method as set forth in claim 5 wherein magnetic resonance images of blood flow and perfusion are enhanced.

10. A method as set forth in claim 5 wherein magnetic resonance images of the kidney are enhanced.